US006759208B2

(12) United States Patent
Winther et al.

(10) Patent No.: US 6,759,208 B2
(45) Date of Patent: Jul. 6, 2004

(54) HIGH THROUGHPUT SCREENING ASSAYS USING FATTY ACID SYNTHETIC ENZYMES

(75) Inventors: Michael D. Winther, Vancouver (CA); Mark P. Gray-Keller, Middleton, WI (US)

(73) Assignee: Xenon Genetics Inc., Burnaby (CA)

( * ) Notice: Subject to any disclaimer, the term of this patent is extended or adjusted under 35 U.S.C. 154(b) by 0 days.

(21) Appl. No.: 10/232,732

(22) Filed: Aug. 29, 2002

(65) Prior Publication Data

US 2003/0129129 A1 Jul. 10, 2003

Related U.S. Application Data

(60) Provisional application No. 60/315,763, filed on Aug. 29, 2001.

(51) Int. Cl.$^7$ .......................... C12Q 1/36; A61M 36/14; A01N 61/00

(52) U.S. Cl. ............................. 435/25; 424/1.11; 514/1

(58) Field of Search ........................... 424/1.11; 435/25; 514/1

(56) References Cited

U.S. PATENT DOCUMENTS

| 5,336,496 A | 8/1994 | Akimoto et al. |
| 5,443,974 A | 8/1995 | Hitz et al. |

FOREIGN PATENT DOCUMENTS

| WO | WO 00/09754 | 2/2000 |
| WO | WO 01/62954 | 8/2001 |

OTHER PUBLICATIONS

Choi, et al., "The trans–10, cis–12 Isomer of Conjugated Linoleic Acid Downregulates Stearoyl–CoA Desaturase 1 Gene Expression in 3T3–L1 Adipocytes," J. Nutrition, vol. 130, pp. 1920–1924 (2000).
Zoeller, et al., "The Importance of the stearoyl–CoA desaturase system in octadecenoate metabolism in the Morris hepatona7288C," Biochim. Biophys. Acta, vol. 845, pp. 380–388 (1985).
Bretillon, et al., "Effects of Conjugated Linoleic Acid Isomers on the Hepatic Microsomal Desaturation Activities in Vitro," Lipids, vol. 24, No. 9, pp. 965–969 (1999).
Hovik, et al., "Thia fatty acids as substrates and inhibitors of stearoyl–CoA desaturase," Biochim. Biophys. Acta, vol. 845, pp. 251–256 (1997).
Khoo, et al., "Manipulation of body fat composition with sterculic acid can inhibit mammary carcinomas in vivo," British J. Cancer, vol. 63, pp. 97–101 (1991).
Cao, et al., "Inhibition of fatty acid Δ6– and Δ5–desaturation by cyclopropene fatty acids in rat liver microsomes," Biochim. Biophys. Acta, vol. 1210, pp. 27–34 (1993).

Park, et al., "Inhibition of hepatic stearoyl–CoA desaturase activity by trans–10, cis–12 conjugated linoleic acid and its derivatives," Biochim. Biophys. Acta, vol. 1486, pp. 285–292 (2000).
de Antueno, et al., "Relationship Between Mouse liver Δ9 Desaturase Activity," Lipids, vol. 28, No. 4, (1993).
Legrand, et al., "Inhibiting Δ9–Desaturase Activity Impairs Triacylglycerol Secretion In Cultured Chicken Hepatocytes" J. Nutrition, vol. 127, pp. 249–256 (1997).
Ntambi, J.M., "Regulation of Stearoyl–CoA Desaturase by Polyunsaturated Fatty Acids and Cholesterol", J. Lipid Res. vol. 40, pp. 1549–1558 (1999).
Grinari, et al., "Conjugated Linoleic Acid is Synthesized Endogenously in Lactating Dairy Cows by Δ9–Desaturase," J. Nutrition, vol. 130, pp. 2285–2291, (2000).
Jeffcoat, et al., "Studies on the Inhibition of the Desaturases by Cyclopropenoid Fatty Acids," Lipids, vol. 12, pp. 480–485 (1977).
Jeffcoat, et al., "Interrelationship between the Dietary Regulation of Fatty Acid Synthesis and the Fatty Acyl–CoA Desaturases," Lipids, vol. 12, pp. 469–474 (1977).
Kaestner, et al., "Differentiation–induced Gene Expression in 3T3–L1 Preadipocytes," Journal of Biological Chemistry, vol. 264, No. 25, pp. 14755–14761 (1991).
Ntambi, "Scd1 is expressed in sebaceous glands and is disrupted in the asebia mouse," Nature Genetics, vol. 23, p. 268 (1999).
Ntambi, "Regulation of stearoyl–CoA desaturase by polyunsaturated fatty acids and cholesterol," Journal of Lipid Research, vol. 40, pp. 1549–1558 (1999).
Legrand, et al., "Hepatic Δ9 desaturation and plasma VLDL level in genetically lean and fat chickens,"International Journal of Obesity, vol. 16, pp. 289–294 (1992).
Legrand et al., "Stearoyl–CoA Desaturase Activity in Primary Culture of Chicken Hepatocytes. Influence of Insulin, Glucocorticoid, Fatty Acids and Cordycepin," Int'l. J. Biochem, vol. 26, No. 6, pp. 777–785 (1994).
Lefevre, et al., "Hormonal Regulation of Stearoyl Coenzyme–A Desaturase 1 Activity and Gene Expression in Primary Cultures of Chicken Hepatocytes," Archives of Biochemistry and Biophysics, vol. 368, No. 2, pp. 329–337 (Aug. 15, 1999).
Legrand, et al., Effect of Insulin on Triacylglycerol Synthesis and Secretion by Chicken Hepatocytes in Primary Culture, Int'l. J. Biochem Cell Bio., vol. 28, No. 4, pp. 431–440 (1996).

(List continued on next page.)

*Primary Examiner*—Jon P. Weber
*Assistant Examiner*—Kailash C. Srivastava
(74) *Attorney, Agent, or Firm*—Elliott M. Olstein; Alan J. Grant (57) ABSTRACT

High throughput screening assays for the identification of potential therapeutic agents able to modulate the activity of enzymes of fatty acid biosynthesis, especially desaturases and/or elongases, are disclosed along with therapeutic uses of the agents identified by such assays for the prevention and/or treatment of diseases related to fatty acid metabolism. Substrates useful in such assays are also described.

12 Claims, 3 Drawing Sheets

OTHER PUBLICATIONS

Li, et al., "Partial Characterization of a cDNA for Human Stearoyl–CoA Desaturase and Changes in its mRNA Expression in Some Normal and Malignant Tissues," Int'l J. Cancer, vol. 57, pp. 348–352 (1994).

Park et al., "Lipid Level and Type Alter Stearoyl CoA Desaturase mRNA Abundance Differently in Mice with Distinct Susceptibilities to Diet–Influenced Diseases", J. Nutrition, vol. 127, pp. 566–573 (1997).

Waters et al., "Localization of a Negative Thyroid Hormone–Response Region in Hepatic Stearoyl–CoA Desaturase Gene 1", Biochem. Biophys. Res. Comm., vol. 233, pp. 838–843, (1977).

Zhang et al., "Human Stearoyl–CoA Desaturase: Alternative Transcripts Generated from a Single Gene by Usage of Tandem Polyadenylation Sites", Biochem J., vol. 340, pp. 255–264 (1999).

Database Biosis Online. Waters & Ntambi: "Polyunsaturated Fatty Acids Inhibit Hepatic Stearoyl–CoA Desaturase–1 Gene in Diabetic Mice", vol. 31, No. Suppl., pp. S33–S36 (1996), Accession No. PREV 199698795704.

Kurebayashi S. et al., "Thiazolidinediones Downregulate Stearoyl–CoA Desaturase 1 Gene Expression in 3T3–L1 Adipocytes", Diabetes, vol. 46, pp. 2115–2118, Dec. 1997.

Singh & Ntambi, "Nuclear Factor 1 is Essential Fir the Expression of Stearoyl–CoA Desaturase 1 Gene During Preadipocyte Differentiation", Biochim. Biophys. Acta., vol. 1398; 1998, pp. 145–156.

Sessler et al., "Regulation of Stearoyl–CoA Desaturase 1 mRNA Stability by Polyunsaturated Fatty Acids in 3T3–L1 Adipocytes", J. Biol. Chem., vol. 271, No. 47, pp. 29854–29858 (Nov. 22, 1996.).

HIGH THROUGHPUT SCREENING ASSAYS USING FATTY ACID SYNTHETIC ENZYMES

This application claims priority of U.S. Provisional Application Serial No. 60/315,763, filed Aug. 29, 2001, the disclosure of which is hereby incorporated by reference in its entirety.

FIELD OF THE INVENTION

The present invention relates to high throughput screening assays for the identification of potential therapeutic agents and to uses of agents identified by such assays for the prevention and/or treatment of diseases related to fatty acid metabolism.

BACKGROUND OF THE INVENTION

Acyl desaturase enzymes catalyze the formation of double bonds in fatty acids derived from either dietary sources or de novo synthesis in the liver. Mammals synthesize at least three distinct desaturases, which catalyze desaturation fatty acids at different positions. These enzymes are referred to by the carbon number at which the double bond is inserted, which may occur at the Δ9, Δ6 and Δ5 positions. The resulting mono-unsaturated or polyunsaturated fatty acids are substrates for incorporation into phospholipids, triglycerides, and cholesterol esters.

In human and other mammalian cells, microsomal Δ6 desaturation of the essential fatty acids linoleic acid (18:2n-6) and alpha-linolenic acid (18:3n-3) is an initial and rate limiting step in the biosynthesis of both n-6 and n-3 polyunsaturated fatty acids (PUFAs). The microsomal fraction is the fraction, comprising microspheres and other structures, produced by break-up of the rough endoplasmic reticulum following ultracentrifugation and represents a readily producible form of a number of key cellular enzymes. The products of the aforementioned reactions are gammalinolenic (18:3n-6) and stearidonic acids (18:4n-3) which are subsequently elongated to dihomogammalinolenic acid (DGLA) (20:3n-6) and to the 20:4n-3 product, respectively. The resulting fatty acids are utilized as substrates of a Δ5 desaturase that generates arachidonic acid (20:4n-6) and 20:5n-3. The latter are then further elongated to 22:4n-6 and 22:5n-3, respectively, and finally used to form the products 24:4n-6 and 24:5n-3. The delta-5 desaturase that produces 20:3n9 (or Mead acid) may not be the same enzyme that produces arachidonic acid from DGLA.

In addition to the foregoing, a second microsomal Δ6 desaturation occurs on the PUFAs. The products of this desaturation, 24:5n-6 and 24:6n-3, are converted to 22:5n-6 and 22:6n-3, respectively, by peroxisomal β-oxidation (Sprecher, H. (2000) Biochim. Biophys. Acta. 1486, 219–231). In addition, two sequential elongations of 20:4n-3 (i.e., 22:4n-3 and 24:4n-3) were described by Sauerwald et al. as part of putative alternative steps in the synthesis of 22:6n-3 (Sauerwald, T. U., Hachey, D. L., Jensen, C. L., Chen, H., Anderson, R. E. and Heird W. C. (1997) Pediatr. Res. 41, 183–187). These authors proposed that 24:4n-3 could undergo Δ9 desaturation to 24:5n-3 which can act as substrate of the Δ6 desaturase. Direct elongations on 18:2n-6, 18:3n-3 and 20:3n-6 are also reported.

Evidence shows that the Δ6 desaturase, which recognizes 18-carbon unsaturated fatty acids (18:2n-6 or 18:3n-3), is the same enzyme that desaturates 24-carbon substrates (De Antueno, R. J., Knickle, L C, Smith, H., Elliot, M. L., Allen, S. J., Nwaka, S., and Winther, M. D. (2001) FEBS Letters 509, 77-80, and Innis, S. M., Sprecher, H., Hachey, D., Edmond, J. and Anderson, R. E. (1999) Lipids. 34, 139–149. Cho and coworkers were the first to clone this human Δ6 desaturase and test its activity on the generally used 18-carbon PUFA substrate. (Cho, H. P., Nakamura, M. T. and Clarke, S. D. (1999) J. Biol. Chem. 274, 471–477). In addition, Sauerwald and coworkers (1997) have suggested that two Δ6 desaturation steps active on 18:3n-3 and 18:2n-6 would compete not only with each other but also with 24:5n-3 and 24:4n-6. Sprecher, in a recent review addressing this subject, has emphasized that the control of the Δ6 desaturase would be of considerable interest in animals or human studies if a single enzyme is active on 4 different fatty acids from both n-6 and n-3 families (See: Sprecher, supra).

The delta-6 desaturase carries out desaturation on at least 4 distinct substrates: 18:3n6, 24:4n6, 18:3n3 and 24:5n3. See: De Antueno R J, Knickle L C, Smith H, Elliott M L, Allen S J, Nwaka S, Winther M D, "Activity of human Delta5 and Delta6 desaturases on multiple n-3 and n-6 polyunsaturated fatty acid," *FEBS Lett.* Nov 30;509(1): 77–80 (2001); D'andrea S, Guillou H, Jan S, Catheline D, Thibault J N, Bouriel M, Rioux V, Legrand P., "The same rat Delta6-desaturase not only acts on 18- but also on 24-carbon fatty acids in very-long-chain polyunsaturated fatty acid biosynthesis," *Biochem J* 364(Pt1):49-55 (May 15, 2002). In addition, 18:1n9 (oleic acid) should also be a substrate (although, perhaps, with lower affinity).

There are several different elongases present in mammalian cells, which are active on different fatty acid substrates. Some of these have been characterized (see Winther et al, WO 02/44320). In at least one example a genetic defect in a human elongase is associated with a human disease, indicating the importance of this enzyme family as a therapeutic target (Zhang, K., Kniazeva, M. Han, M. et al (2001) Nature Genetics 27, 89–93).

It has been shown (see Brownlie et al, WO 01/62954) that delta-9 desaturase activity may be indirectly measured in a microsomal assay by measuring the release of tritium from the C9 and C10 positions of stearoyl-CoA, in the form of water. In accordance with the present invention, this kind of assay is applicable to a wide range of other desaturase and elongase enzymes using an efficient and economical tritium based assay. Using the process disclosed herein, modulators of fatty acid or triglyceride metabolism are readily identified.

BRIEF SUMMARY OF THE INVENTION

In one aspect, the present invention relates to a process for identifying a desaturase-modulating agent, comprising:
  a) contacting a compound with a microsome, said microsome comprising a desaturase enzyme activity, in the presence of a substrate comprising a tritium label wherein said label is bound to a desaturase reactive carbon atom and under conditions promoting the desaturation of said substrate at said reactive carbon atom to form a double bond with said reactive carbon atom with release of tritiated water,
  b) detecting production of said tritiated water,
  c) detecting a difference in the amount or rate of production of said tritiated water compared to when the compound of step (a) is not present thereby identifying a modulator of desaturase activity.

In specific embodiments thereof, the modulation may be an increase or a decrease in desaturase activity and may be determined as either a difference in the amount of said tritiated water detected and/or a difference in the rate of production of said tritiated water. In addition, the tritium label may be present on one or both of the desaturase reactive carbon atoms (i.e., the carbon atoms forming the double bond resulting from this desaturation reaction). In preferred embodiments, the desaturase is a delta-5 desaturase or a delta-5 desaturase.

Preferred substrates for delta-5 desaturases include 20 carbon backbone fatty acids, such as a coenzyme A conjugate of dihomogammalinolenic acid (20:3n6, DGLA), 20:4n3 and 20:2n9, especially where the tritium label is on carbon atom 5 and 6 of the substrate.

Preferred substrates for the delta-6 desaturase include a substrate that is a coenzyme A conjugate of a fatty acid having a backbone of 18 carbon atoms or 24 carbon atoms in length, preferably a coenzyme A conjugate of α-linolenic acid (18:3n3), 24:5n3, linoleic acid (18:2n6), 18:1n9 or 24:4n6, especially where the tritium label is on carbon atom 6 and 7 of the substrate.

In another aspect, the present invention relates to a process for identifying an elongase- and/or desaturase-modulating agent, comprising:
  a) contacting a compound with a microsome, said microsome having a desaturase enzyme activity, in the presence of an elongase and a substrate of said elongase, wherein said substrate is not a substrate of said desaturase enzyme activity, under conditions promoting elongation of said substrate to form an elongated product wherein said product is a substrate of said desaturase and comprises a tritium label bound to a desaturase reactive carbon atom and under conditions promoting desaturation of said substrate of said desaturase to form a double bond involving said desaturase reactive carbon atom with release of tritiated water,
  b) detecting production of said tritiated water,
  c) detecting a difference in the amount or rate of production of said tritiated water compared to when the compound of step (a) is not present, thereby identifying a modulator of elongase and/or desaturase activity.

Preferred embodiments include wherein said modulation is a decrease or increase in desaturase and/or elongase activity, preferably where the desaturase is a delta-5 desaturase and where the substrate for the elongase is a 16, 18, 20 or 22-carbon atom backbone fatty acid.

Substrates of the elongase may also be substrates of the n9 pathway (which starts with oleic acid 18:1n9) and the n7 pathway (which starts with palmitic acid (16:0). Elongation substrates would be: 18:2n9, 20:3n9, 18:1n9, 20:1n9, 22:1n9, 16:0, 16:1n7, 18:1n7, 20:1n7.

In a further aspect, the present invention relates to a process for identifying an elongase-modulating agent, comprising:
  a) contacting a compound with a microsome, said microsome having a desaturase enzyme activity, in the presence of an elongase and a substrate of said elongase, wherein said compound is not a modulator of said desaturase activity using the process disclosed herein without the elongase for determining modulators of desaturase activity and wherein said substrate is not a substrate of said desaturase enzyme activity, under conditions promoting elongation of said substrate to form an elongated product wherein said product is a substrate of said desaturase and comprises a tritium label bound to a desaturase reactive carbon atom and under conditions promoting desaturation of said substrate of said desaturase to form a double bond involving said desaturase reactive carbon atom with release of tritiated water,
  b) detecting production of said tritiated water,
  c) detecting a difference in the amount or rate of production of said tritiated water compared to when the compound of step (a) is not present, and thereby identifying a modulator of elongase activity.

Preferred embodiments include wherein said modulation is a decrease or increase in desaturase and/or elongase activity, preferably where the desaturase is a delta-5 desaturase and where the substrate for the elongase is an 18, 20 or 22-carbon atom backbone fatty acid.

Substrates of the elongase again would include substrates of the n9 pathway (which starts with oleic acid 18:1n9) and the n7 pathway (which starts with palmitic acid (16:0). Elongation substrates would be: 18:2n9, 20:3n9, 18:1n9, 20:1n9, 22:1n9,16:0, 16:1n7, 18:1n7, 20:1n7.

In an additional aspect, the present invention relates to a process for identifying a therapeutic agent useful in modifying fatty acid levels to bring about therapeutic interventions in a range of diseases, comprising identifying an agent according to the modulator-determining processes of the invention and further comprising administering said agent to an animal and then detecting a decrease in said triglyceride levels following said administration thereby identifying such a therapeutic agent. Preferred embodiments thereof include where the animal is afflicted with metabolic disorders with altered fatty acid metabolism, most preferably where said animal is a human being.

In a still further aspect, the present invention relates to a process for treating a disease of fatty acid metabolism in an animal comprising administering to an animal afflicted therewith a therapeutically effective amount of a compound first identified as a desaturase and/or elongase modulating agent using an assay as disclosed herein according to the invention, especially where said animal is a human being.

In a yet further aspect, the present invention relates to a process for protecting an animal against a disorder involving fatty acid metabolism comprising administering to an animal predisposed to developing such a disorder a therapeutically effective amount of a compound first identified as a desaturase and/or elongase modulating agent using an assay of the invention, preferably where said animal is a human being, most preferably a human genetically predisposed to develop said disorder.

In a yet still further aspect, the present invention relates to a method for producing a product comprising identifying an agent according to any of the assay processes of the invention wherein said product is the data collected with respect to said agent as a result of said process and wherein said data is sufficient to convey the chemical structure and/or properties of said agent.

DETAILED DESCRIPTION OF THE INVENTION

This invention relates to high throughput screening assays and their methods of use in identifying potential therapeutic agents, especially where such assays employ a microsomal source of enzymes, both desaturase and elongase enzymes.

The assays of the invention identify modulators of specific plant or animal desaturases and elongases that are involved in fatty acid synthesis. All assays measure the release of tritium, in the form of water, from fatty acid substrates that have been tritiated at the specific site of desaturation which is recognized by the specific desaturase or elongase in question. Each assay is a simple and highly effective high throughput assay that are useful for the identification of modulators, specifically small molecule modulators, of the specific desaturase or elongase. These modulators and their analogs have potential therapeutic activity in a wide variety of human diseases, as described below.

Known enzymes in this pathway include Human Δ5 desaturase (Genbank Accession No. AF226273), Human Δ6 desaturase (Genbank Accession Nos. AF126799) and those listed in Mukerji et al. (WO 00/12720) as well as the new human elongases are found in "Human Elongase Genes, Uses Thereof, and Compounds for Modulating Same" (see Winther et al, WO 02/44320), the disclosure of which is hereby incorporated by reference in its entirety.

It should be well noted that the enzymes useful in the assays of the invention have strict substrate specificities. Thus, in accordance with the present invention, by adding the proper tritiated substrate, modulators of the enzyme that uses that substrate are readily identified.

The presence of an asterisk (*) indicates the presence of a tritium label. In all cases the tritium label is located at the positions where the desaturation reaction takes place. Table 1 describes the substrate specificity enzymes assayed according to the present invention.

Preferred assays of this invention are rat or mouse liver microsomal assays spiked with the specific tritiated substrate.

TABLE 1

| Enzyme Assay | Radio-labeled Ligand | Comment |
| --- | --- | --- |
| Delta-5 desaturase | For delta-5-desaturase the substrate may be the CoA conjugate of dihomogamma linolenic acid 20:3n6 (8, 11, 14-eicosatrienoic acid), 20:4n3 or 20:2n9. Positions of label are: DGLA 20:3n6, 20:4n3 or 20:2n9 $^3$H on C5* and C6* | Delta-5 works principally on a 20 carbon substrate. |
| Elongase | Various substrates possible. Example: GLA 18:3n6-$^3$H on C3 and C4 is elongated to 20:3n6 which is a substrate for desaturation by delta-5 desaturase. Or EPA 20:5n3 is elongated to 22:5 n6 and then to 24:5n6, the EPA being labeled on C2 and C3 for the two elongation steps. The $^3$H is released when the 24:5 is desaturated by D6D. | Example: Since Delta-5 works principally on substrates with 20 carbons, by adding labeled 18 carbon subst-, rate, the desaturation only occurs to the extent of of success of the elongase reaction. Thus modulators of elongase are identifiable. |
| Delta-6 desaturase | For delta-6-desaturase the substrate may be the CoA conjugate of linoleic acid, 18:2n6 (6, 9, 12-octadecadienoic acid) or alpha-linolenic acid 18:3n3 (9, 12, 15-octadecatrienoic acid), 24:4n6, 24:5n3 or 18:1n9. Linoleic acid 18:2n6-$^3$H on C6* and C7* | Works on selected 18-C or 24C substrates, but not on 20C substrates. thus the $^3$H on C6 will not measure delta 5 activity. |

TABLE 1-continued

| Enzyme Assay | Radio-labeled Ligand | Comment |
| --- | --- | --- |
| | or 24:4n6-$^3$H on C6* and C7* or 24:5n3-$^3$H on C6* and C7* or 18:3n3-$^3$H on C6* and 07* | |

Abbreviations used in Table 1 are: GLA=gamma-linolenic acid; EPA=eicosapentanoic acid; DGLA=dihomogamma-linolenic acid, * means tritium: $^3$H—.

In accordance with the foregoing, the present invention relates to a process for identifying a desaturase-modulating agent, comprising:

a) contacting a compound with a microsome, said microsome comprising a desaturase enzyme activity, in the presence of a substrate comprising a tritium label wherein said label is bound to a desaturase reactive carbon atom and under conditions promoting the desaturation of said substrate at said reactive carbon atom to form a double bond with said reactive carbon atom with release of tritiated water, b) detecting production of said tritiated water, c) detecting a difference in the amount or rate of production of said tritiated water compared to when the compound of step (a) is not present thereby identifying a modulator of desaturase activity.

In particular embodiments of this process, the modulation may be an increase or a decrease in the desaturase activity and includes embodiments wherein the difference of step (c) is a difference in the amount of said tritiated water detected and/or a difference in the rate of production of said tritiated water. For example, if an inhibitor is an irreversible inhibitor of the enzyme, the reaction may not go to completion so that the amount of tritiated water detected following a specific time period of said reaction is less than where the compound to be tested is not present. Alternatively, where said compound is a competitive or non-competitive inhibitor of the desaturase, the reaction kinetics may be temporally different but the overall production of tritiated water may be the same. In addition, the detection of tritiated water within the processes of the invention may be qualitative or quantitative so that actual amounts of product may be measured or reaction in the presence of a compound to be tested for modulating activity may be compared to cases where the compound is not present. Further, measurements of production of tritiated water may be used to compare the activity of one test compound against another. For example, should one compound cause a decrease in the rate of production of tritiated water that is twice the decrease produced by a second compound, the first compound may be deemed within the invention to be twice as effective in modulating, or inhibiting, the enzyme as the second compound. By screening a series of test compounds, the most advantageous one can be found.

A substrate for desaturation will of course be converted to a product that contains a carbon-carbon double bond. The carbon atoms in this substrate that form this double bond as a result of reaction with the desaturase are referred to herein as the desaturase reactive carbon atoms. It is one, or both, of these carbon atoms that contains the tritium label where tritium replaces one of the hydrogens on the otherwise saturated carbon atom. Thus, in one embodiment of the invention the tritium label is attached to only one of the reactive carbon atoms of a substrate molecule while in a separate embodiment the tritium label is attached to two reactive carbon atoms of the same substrate molecule. Neither of these embodiments serves to limit the overall utility of the invention disclosed herein.

In other specific embodiments of the processes of the present invention, the desaturase is a delta-5 desaturase. In a further embodiment, the substrate is a coenzyme A conjugate of a fatty acid having a backbone of length 20 carbon atoms, such as where the desaturase is a delta-5 desaturase. In preferred embodiments, the substrate of said desaturase is a substrate described herein, such as in Table 1, especially where the substrate is a coenzyme A conjugate of a member selected from the group consisting of dihomogammalinolenic acid, DGLA (20:3 n6), 20:2n9 and 20:4n3. In specific embodiments thereof, the tritium label is on carbon atom 5 and 6 of the substrate.

In a further embodiment of the processes of the invention, the desaturase is a delta-6 desaturase. In other embodiments thereof, the substrate is a coenzyme A conjugate of a fatty acid having a backbone of 18 carbon atoms or 24 carbon atoms in length. In a preferred embodiment, the substrate is one as recited herein, such as one of those of Table 1, preferably where the substrate is a coenzyme A conjugate of a member selected from the group consisting of linoleic acid (18:2n6), alpha-linolenic acid (18:3n3), oleic acid (18:1 n9), 24:4n6 and 24:5n3. In a highly preferred embodiment thereof, the tritium label is on carbon atom 6 and 7 of the substrate.

The present invention further relates to a process for identifying an elongase- and/or desaturase-modulating agent, comprising:

a) contacting a compound with a microsome, said microsome having a desaturase enzyme activity, in the presence of an elongase and a substrate of said elongase, wherein said substrate is not a substrate of said desaturase enzyme activity, under conditions promoting elongation of said substrate to form an elongated product wherein said product is a substrate of said desaturase and comprises a tritium label bound to a desaturase reactive carbon atom and under conditions promoting desaturation of said substrate of said desaturase to form a double bond involving said desaturase reactive carbon atom with release of tritiated water, b) detecting production of said tritiated water, c) detecting a difference in the amount or rate of production of said tritiated water compared to when the compound of step (a) is not present, thereby identifying a modulator of elongase and/or desaturase activity.

In a particular embodiment of such process, the modulation is a decrease in desaturase and/or elongase activity or an increase in desaturase and/or elongase activity. In other preferred embodiments, said difference of step (c) is a difference in the amount of said tritiated water detected or a difference in the rate of production of said tritiated water as described hereinabove and wherein said tritium label is attached to only one desaturase reactive carbon atom of a substrate molecule or is attached to two desaturase reactive carbon atoms of the same substrate molecule. In a preferred embodiment, the desaturase is a delta-5 desaturase. In another preferred embodiment, the substrate of said elongase comprises a 16, 18, 20 or 22-carbon atom backbone fatty acid, most preferably 18 carbons.

Substrates of the elongase may also be substrates of the n9 pathway (which starts with oleic acid 18:1n9) and the n7 pathway (which starts with palmitic acid (16:0). Preferred elongation substrates would be: 18:2n9, 20:3n9, 18:1n9, 20:1n9, 22:1n9, 16:0, 16:1n7, 18:1n7, 20:1n7. It should be noted that for the EPA substrate noted in Table 1 (and labeled at C2 and C3) the substrate must undergo two sequential elongations and a delta-6 desaturation to release the tritiated water product. In such an assay, either step could be inhibited by a test compound but the overall result would be to produce a relatively small number of compounds for further screening.

A variety of synthetic routes for making the tritiated substrates required for this invention are known to those skilled in the art. An example is the DGLA substrate employed in the delta-5 desaturase reaction. This 20:3n-6 fatty acid requires a tritium atom on the C5 and C6 carbons (counting from the COOH or CoA head group) in order to measure the delta-5 desaturation step to form arachadonic acid (AA). The techniques include enzymatic retroconversion of AA-CoA in the presence of tritiated water and delta-5 desaturase. This reaction simply employes the reversible enzymatic activity of delta-5 desaturase, and is driven by excess AA-CoA and also plant, algal or microbe based synthesis in the presence of tritiated malonyl-CoA. In this reaction, an algae, plant cell or microbe (or an extract thereof) is presented with a C14:0 substrate and tritiated malonyl-CoA. Natural enzymes in these organisms will extend the chain to creat C16:0, C18:0, C18:1 and C18:2 substrates. After sufficient time to generate the C16:0, the reaction is flooded with cold (or un-tritiated) malonyl-CoA. The chain extension continues with cold malonyl-CoA. The resulting C18:2 product is then exposed to a delta-6 desaturase and an elongase to generate DGLA with a predominance of tritiums at the C5-C6 carbons. In addition, total synthesis of fatty acids has been explored by several groups. Though yields are low, it is possible to generate a DGLA from 2 carbon substrates, adding in a tritiated pair of carbons at the C5-C6 carbons. It is also possible to use DGLA that is tritiated at all carbons. This substrate is commercially available. When employed in a microsome extract containing an abundance of delta-5 desaturase activity, the predominant and perhaps exclusive reduction takes place at C5-C6. There may generally be a higher level of background when using a fully tritiated substrate, but assay conditions can be optimized by those skilled in the art to distinguish delta-5 desaturase activity from other reactions. Useful synthetic procedures are also found in U.S. Pat. No. 6,441,035 (Aug. 27, 2002) the disclosure of which is hereby incorporated by reference in its entirety.

As used herein, the meaning of "delta-5 desaturase", "delta-6 desaturase" and/or "elongase" in respect to screening assays should be taken to include all functional variants of the underlying genes or proteins (depending on use), including all known or yet to be discovered alleles, variants, polymorphisms or mutants of such genes/proteins, and especially including all orthologs and homologs from different species such as the human, mouse or rat forms disclosed previously, forms from other mammals, other vertebrates, and those forms found in invertebrates and single cell organisms, viruses and the like. Of course, screening assays need to employ an enzyme which has the required biological activity in order to identify compounds which inhibit that activity. These compounds that are therapeutic agents of the invention, or analogs thereof. In a preferred embodiment, the screening assay employs a mammalian form of the gene, such as a microsomal extract of a mammalian cell or a recombinant cell transformed with a plasmid expression construct containing a functional form of the gene. Those skilled in the art know how to identify such variants and orthologs from public databases of gene/protein sequence (i.e. GenBank); or alternatively can prepare microsomal extracts from cells of animals where the exact sequence of the gene/protein is not yet known.

Figure 1:
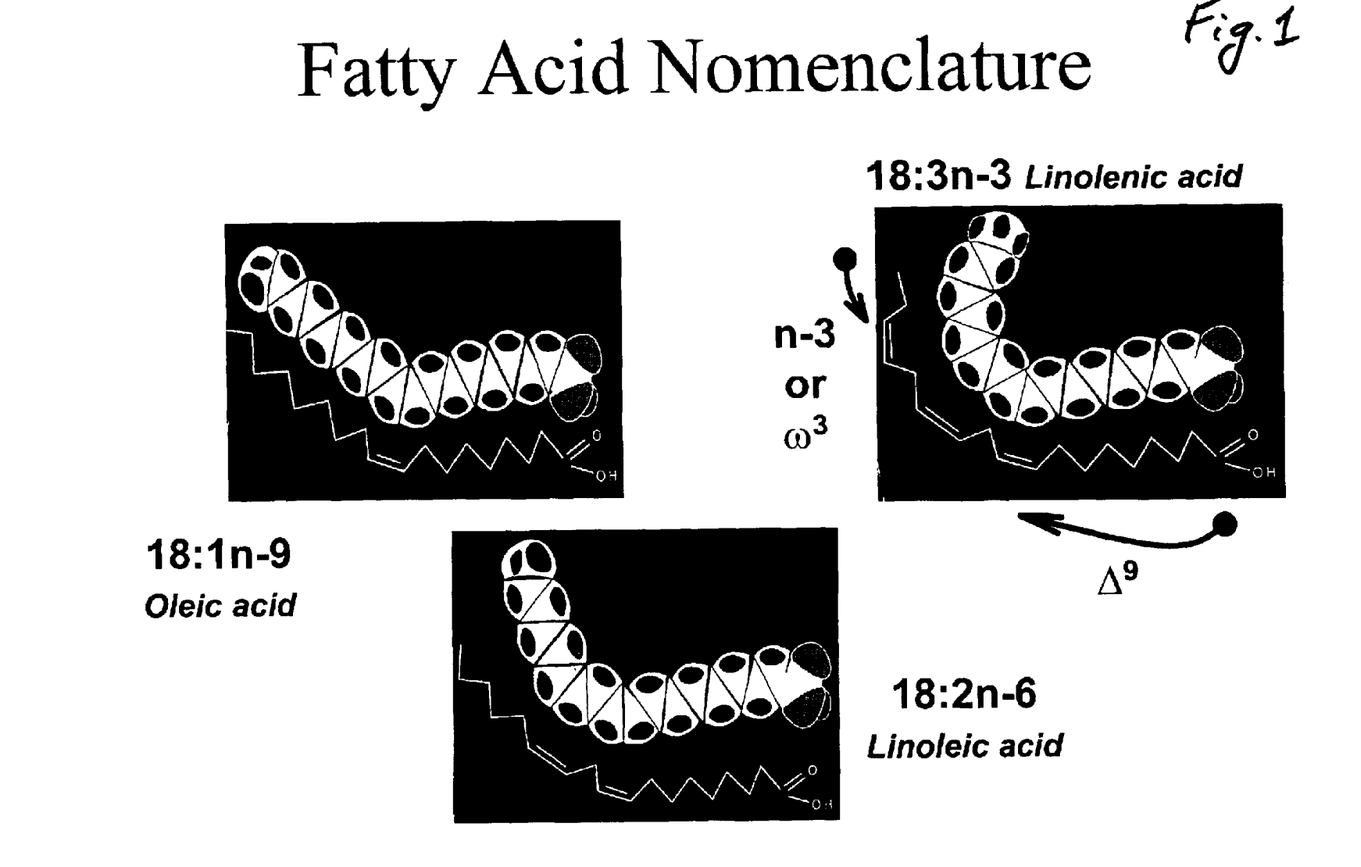
FIG. 1 sets out the nomenclature employed herein to describe specific fatty acids.
Figure 2:
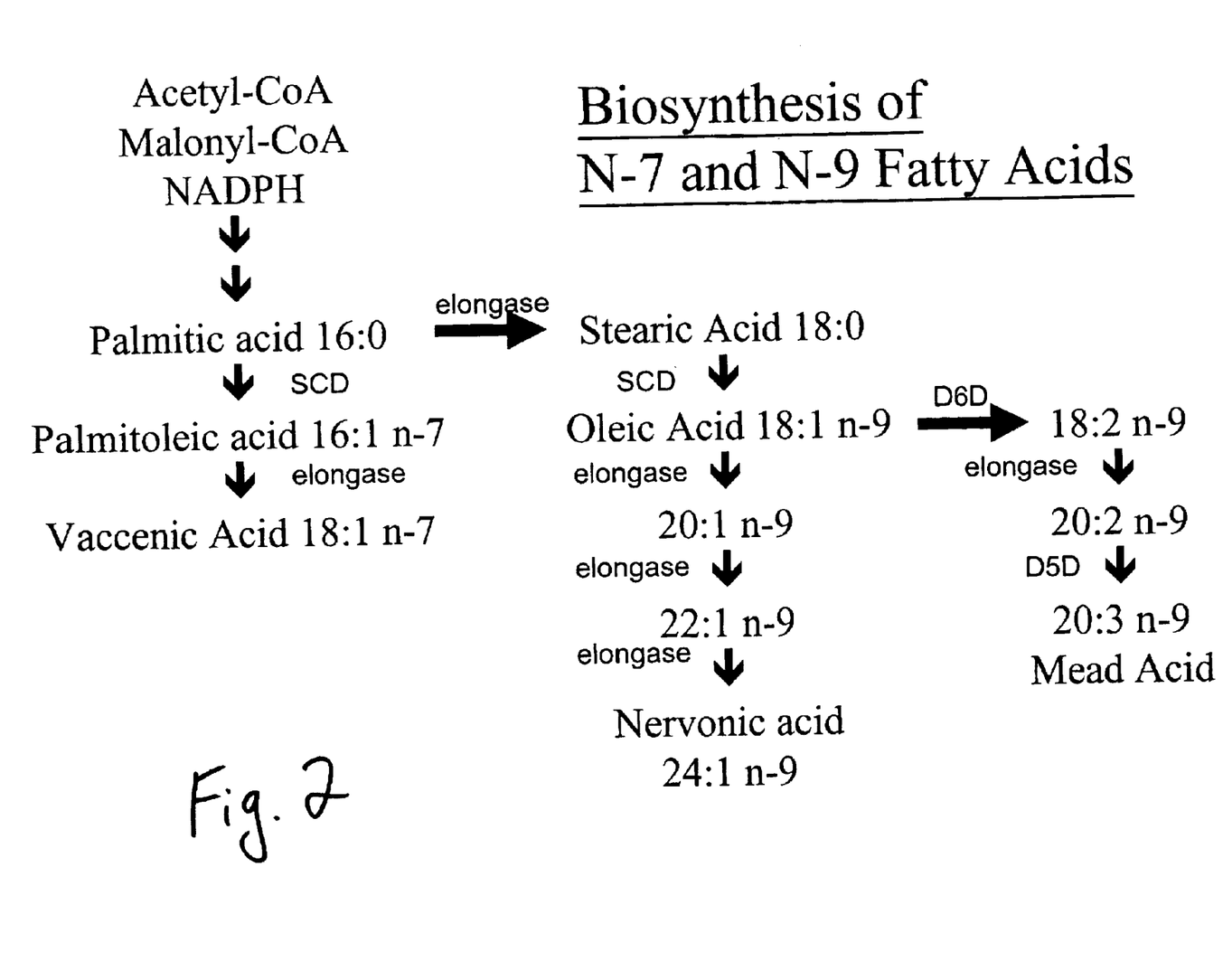
FIG. 2 sets out the steps involved in the biosynthesis of human N-7 and N-9 Fatty Acids FIG. 3 sets out key steps and associated enzymes in human biosynthesis of N-3 and N-6 Poly-Unsaturated Fatty Acids (PUFAs).
Figure 3:
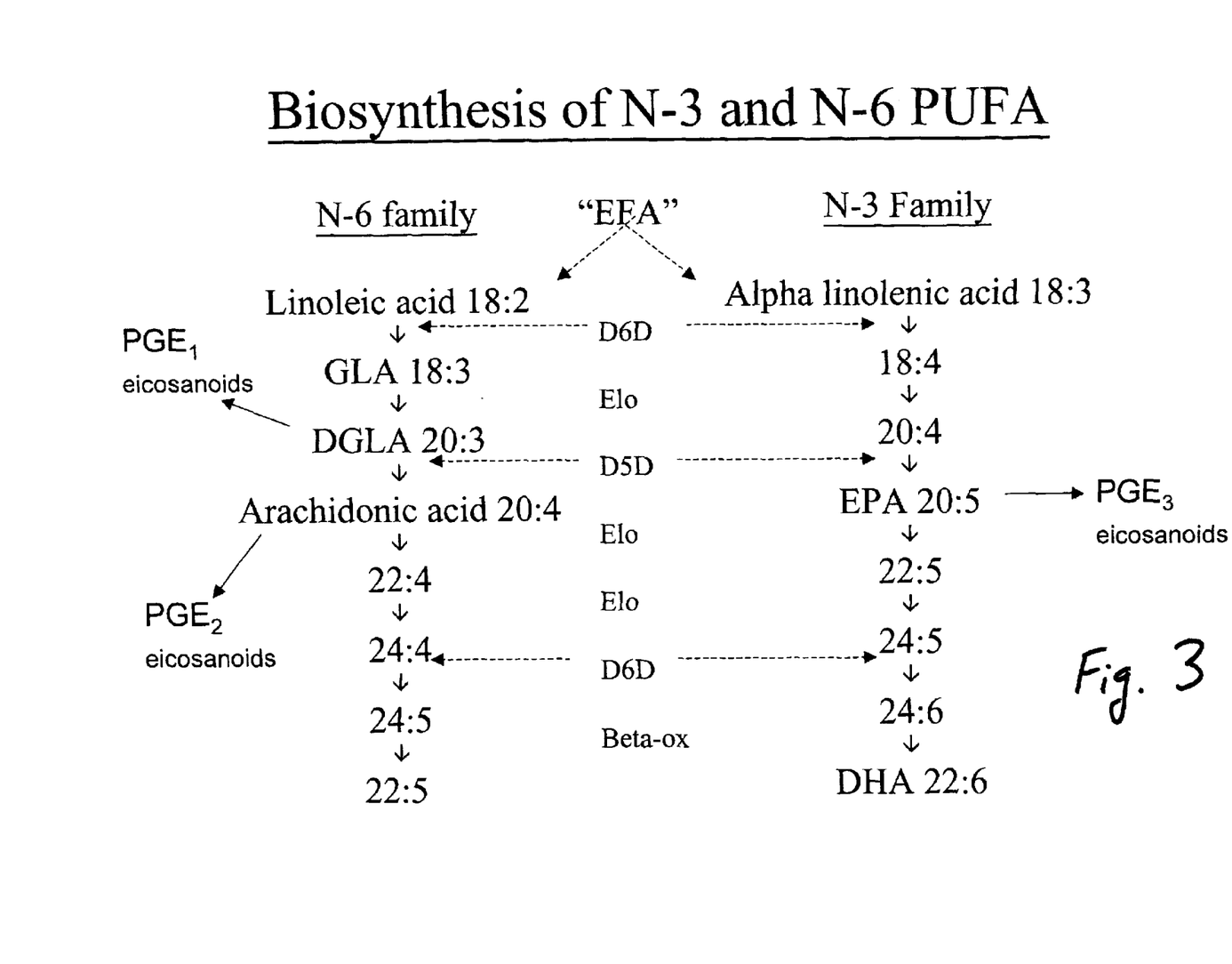

The present invention has a number of therapeutic uses because compounds that modulate enzymes of fatty acid metabolism are useful in controlling the deleterious effects of a host of diseases caused by, or related to, disorders of fatty acid metabolism, such as the many diseases related to triglyceride metabolism. A non-limiting summary of diseases and disorders which are known in the art to relate to the fatty acid metabolism pathways controlled by delta-5 desaturase, delta-6 desaturase and elongases (for example, those in FIG. 2 and FIG. 3) and for which the compounds identified by the screening assays of this invention may be used, is: inflammation, pain, analgesia, vascular disease and cardiovascular disease, dyslipidemia, diabetes (Type I or Type II), obesity, metabolic disease, metabolic syndrome, and skin disorders (including skin cancer). These broad categories cover a wide range of specific diseases and disorders known to those in the art.

The present invention further relates to a process for identifying an elongase-modulating agent, comprising:

a) contacting a compound with a microsome, said microsome having a desaturase enzyme activity, in the presence of an elongase and a substrate of said elongase, wherein said compound is not a modulator of said desaturase activity using the process of claim 1 and wherein said substrate is not a substrate of said desaturase enzyme activity, under conditions promoting elongation of said substrate to form an elongated product wherein said product is a substrate of said desaturase and comprises a tritium label bound to a desaturase reactive carbon atom and under conditions promoting desaturation of said substrate of said desaturase to form a double bond involving said desaturase reactive carbon atom with release of tritiated water, b) detecting production of said tritiated water, c) detecting a difference in the amount or rate of production of said tritiated water compared to when the compound of step (a) is not present, and thereby identifying a modulator of elongase activity.

As described elsewhere herein, embodiments include cases where the modulation is a decrease in desaturase and/or elongase activity or is an increase in desaturase and/or elongase activity, wherein said difference of step (c) is a difference in the amount of said tritiated water detected or a difference in the rate of production of said tritiated water and wherein said tritium label is attached to only one desaturase reactive carbon atom of a substrate molecule or is attached to two desaturase reactive carbon atoms of the same substrate molecule.

In a preferred embodiment of this process, the desaturase is a delta-5 or delta-6 desaturase. In a highly preferred embodiment, the substrate of said elongase comprises a fatty acid having a backbone of 18 carbon atoms so that the product has a backbone of 20 carbon atoms (since delta-5 desaturases generally only utilize 20 carbon atom fatty acids as substrates). Of course, this in no way limits the utility of the invention for detecting modulators of elongase activity since the substrate for the elongase may have any number of carbons, generally an even number, so long as the desaturase used in the assay accepts as substrate the corresponding product of the elongase.

Other substrates of the elongase include 16, 18, 20 and 22 carbon atom backbone fatty acids, especially 18 carbon atoms. Substrates of the elongase may again be substrates of the n9 pathway (which starts with oleic acid 18:1n9) and the n7 pathway (which starts with palmitic acid (16:0), with preferred elongation substrates would be: 18:2n9, 20:3n9, 18:1n9, 20:1n9, 22:1n9, 16:0, 16:1n7, 18:1n7, 20:1n7

Alternatively, such agents can be utilized in the prevention of onset of such disorders, especially in an animal, preferably a human, predisposed, genetically or otherwise, to develop such disorders at some time during the life of said animal. Thus, the present invention also relates to a process for identifying a therapeutic agent useful in reducing elevated triglyceride levels comprising identifying a desaturase and/or elongase modulating agent according to a process of the invention and further comprising administering said agent to an animal and then detecting a decrease in said triglyceride levels following said administration thereby identifying such a therapeutic agent. In a preferred embodiment thereof, said animal is an animal afflicted with elevated triglyceride levels. In a highly preferred embodiment, said animal is a human being.

When used for such therapeutic, or even research, purposes, the compounds or other agents identified by the assay processes of the invention will commonly be present, by solution, suspension, or otherwise, in a pharmaceutically acceptable carrier, including any useful diluents or excipients. The pharmaceutical compositions useful herein include any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like. Although intravenous administration is preferred, any appropriate route of administration may be employed, for example, perenteral, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspension; for oral administration, formulations may be in the form of tablets or capsules; and for intranasal formulations, in the form of powders, nasal drops, or aerosols. A thorough discussion of pharmaceutically acceptable carriers, diluents, and other excipients is presented in REMINGTON'S PHARMACEUTICAL SCIENCES (Mack Pub. Co., N.J. current edition). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the invention include ethylenevinyl acetate copolymer particles, osmotic pumps, implantable infusion systems, and liposomes. Formulations for inhalation may contain excipients, or example, lactose, or may be aqueous solutions containing, for example, polyoxyethylene-9-lauryl ether, glycocholate and deoxycholate, or may be oily solutions for administration in the form of nasal drops, or as a gel.

The present invention also relates to a process that comprises a method for producing a product comprising identifying an agent according to one of the disclosed processes for identifying such an agent (i.e., the modulators of desaturase and/or elongase activity disclosed herein, as well as any other modulators of fatty acid metabolism that can be identified using the assays of the present invention) wherein said product is the data collected with respect to said agent as a result of said identification process, or assay, and wherein said data is sufficient to convey the chemical character and/or structure and/or properties of said agent. For example, the present invention specifically contemplates a situation whereby a user of an assay of the invention may use the assay to screen for compounds having the desired enzyme modulating activity and, having identified the compound, then conveys that information (i.e., information as to structure, dosage, etc) to another user who then utilizes the information to reproduce the agent and administer it for therapeutic or research purposes according to the invention. For example, the user of the assay (user 1) may screen a number of test compounds without knowing the structure or identity of the compounds (such as where a number of code numbers are used the first user is simply given samples labeled with said code numbers) and, after performing the screening process, using one or more assay processes of the present invention, then imparts to a second user (user 2), verbally or in writing or some equivalent fashion, sufficient information to identify the compounds having a particular modulating activity (for example, the code number with the corresponding results). This transmission of information from user 1 to user 2 is specifically contemplated by the present invention.

Because the enzymes discussed herein are clinically relevant, the present invention also relates to a method for preventing a lipid-related disease or condition comprising administering to a patient at risk of developing said disease a therapeutically effective amount of an agent that has activity in any of the assays disclosed herein, such as any of the screening procedures of the invention. In a preferred embodiment, the method is one wherein said agent was first identified as having such activity using said assay. Thus, any agents that have, or would have, activity in one or more of the assays of the invention can find use in preventing such disease or condition.

As used herein, the term "disease or condition" relates especially to maladies as recognized by the medical community as well as conditions that for technical reasons may not commonly be explicitly defined or recognized as a "disease," such as the condition of being overweight, or which, because a causative agent has not been identified or etiology described, other than a defined set of symptoms, is considered a syndrome rather than a disease.

The present invention further relates to a method for treating a lipid-related disease or condition comprising administering to a patient afflicted with a lipid-related disease or condition a therapeutically effective amount of an agent that has activity in an assay of the invention. In a preferred embodiment thereof, said agent was first identified as having such activity using said assay.

The lipid-related disease or condition contemplated by the methods of the invention include any of the diseases of fatty acid metabolism. In a preferred embodiment of the present invention, the lipid-related disease or condition to be treated and/or prevented, is a member selected from the group consisting of eczema, cardiovascular, inflammation, Sjögren's syndrome, gastrointestinal disorders, a viral disease, postviral fatigue, a body weight disorder, a psychiatric disorder, cancer, cystic fibrosis, endometriosis, premenstrual syndrome, alcoholism, congenital liver disease, Alzheimer's syndrome, hypercholesterolemia, autoimmune disorders, atopic disorders, acute respiratory distress syndrome, articular cartilage degradation, diabetes and a complication of diabetes.

It should be noted that the disclosures of all publications, including research articles as well as published patent applications, cited herein are deemed to be incorporated by reference in their entirety.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The invention is described in more detail in the following non-limiting examples. It is to be understood that these methods and examples in no way limit the invention to the embodiments described herein and that other embodiments and uses will no doubt suggest themselves to those skilled in the art.

In the following example, the term "fatty acid" refers to the particular fatty acid being utilized as a substrate since the processes of the invention permit a wide range of different substrates to be tested depending on the enzyme activity to be determined (delta-5 or delta-6 desaturase) and the source of tissue. When a fatty acid is chosen it is used for both the tritium label as well as the non-labeled solutions (reagents 5 and 6 as described in the example). The correct choice of fatty acid substrate and the position of the tritium label is critical for the success of the assay. The radio-labeled compounds described here are entirely novel whether as free fatty acids or when conjugated to Coenzyme A.

It should further be noted that multiple elongases exist and that and the disclosed assays can be used for any of these provided that the correct substrate is employed. In addition, a cell or tissue extract can be used as source where the elongase of interest is amply present.

EXAMPLE 1

Large Volume Method for Delta-5 or Delta-6 Desaturase Activity Assay in Liver Microsomes A. Buffers and Reagents 1. 1 M $NaH_2PO_4$
   add 120 gm $NaH_2PO_4$ to ~800 ml water
   bring to 1L volume with water
   store at room temp.
2. 1 M PK buffer
   add 174.18 gm $K_2HPO_4$ to ~800 ml water
   adjusted to pH 7.2 with 1M $NaH_2PO_4$
   bring to 1L volume with water
   dilute this solution 10-fold with water to yield 0.1 M PK buffer
   store at room temp.
3. 10 mM NaAcetate:50% ethanol solution
   add 82.03 gm $NaC_2H_3O_2$ to ~800 ml water
   adjust to pH 5.6 with glacial acetic acid
   bring to 1L volume with water
   dilute this solution 50-fold to yield 20 mM stock; verify pH 5.6
   add 10 ml 20 mM stock to 10 ml 100% ethanol to yield final 10 mM $NaC_2H_3O_2$/50% ethanol solution
   store at room temp.
4. 20 mM NADH (Sigma No. N-8129)
   add 14.213 mg NADH per ml of 0.1 M PK buffer (should be made fresh each day); store stock crystals at −20° C. in desiccator; keep 20 mM solution on ice until use 5. 1.5 mM fatty acid-CoA
   add correct amount of fatty acid to 10 mM $NaC_2H_3O_2$/ 50% ethanol solution (should be made fresh each day); store stock crystal at −20° C.;
   keep 1.5 mM solution on ice until use
6. Fatty acid, $^3$H-labeled, for example as obtained from American Radiolabeled Chemicals. The selection of fatty acid depends on which enzyme is being assayed.
   For delta-6-desaturase the substrate may be the CoA conjugate of linoleic acid (6,9,12-octadecadienoic acid) or alpha-linolenic acid (9,12,15-octadecatrienoic acid), 24:4 n6 or 24:5 n3.
   For delta-5-desaturase the substrate may be the CoA conjugate of dihomogamma linolenic acid (8,11,14-eicosatrienoic acid) or 20:4 n3. In all cases the tritium label is located at the positions where the desaturation reaction takes place.
   use 1-2 μCi/assay point
   stock concentration is 1 mCi/ml
   store at −20° C.; keep on ice while pipetting to minimize evaporation of solvent
7. 10× PBS stock
   To 800 ml water add the following:
      80 gm NaCl
      2 gm KCl
      11.5 gm $Na_2HPO_4$
      2 gm $KH_2PO_4$
   adjust pH to 7.4 with 1M NaOH
   bring to 1L to yield 10× stock
   note: dilute 10× stock 10-fold with distilled water to make 1× PBS medium
   store at room temp.
8. Charcoal solution
   add 100 gm activated charcoal (Sigma No. C-3014) to 1L 1× PBS medium and store at 4° C.; prior to and during use, this must be stirred constantly to keep the charcoal in suspension
9. 6% PCA solution
   add 100 ml 60% stock solution of perchloric acid to 900 ml water store at room temp.
10. Liver microsomes
    stock concentration should be 5 mg total protein/ml of 0.1 M PK buffer and stored at −80° C.; freeze-thaw once to minimize loss of enzyme activity In one embodiment, assays may employ a large volume "Bench" method as follows:

The protocol for the Bench method yields a total volume of 1.1 ml per assay point (0.2 ml reaction, 0.2 ml PCA and 0.7 ml charcoal).

1. Make assay pre-mix with following composition (per assay point):
   4 μl 1.5 mM fatty acid-CoA (0.03 mM final)
   1 μl 1 mCi/ml radioactive $^3$H fatty acid (1 μCi)
   20 μl 20 mM NADH (2 mM final)
   155 μl 0.1 M PK buffer
   To make assay pre-mix for N number of assay points:
      a. multiply reagent volumes by N
      b. multiply resulting products for each reagent by 1.05 to yield a 5% "cushion" (which can be adjusted up or down depending on the accuracy of liquid handling).
2. Add assay pre-mix (180 μl/assay point) to 20 μl of microsomes to initiate reaction
   a. reaction is run at room temp
   b. duration of reaction can range between 5-30 mins
   It is advisable to add "test" compounds to microsomes as a pre-incubation period prior to the addition of assay pre-mix.
3. Add 100 μl of 6% PCA to quench reaction and vortex the sample to mix
4. Add 700 μl of charcoal suspension to sediment the unused substrate
5. Vigorously vortex sample to mix
6. Centrifuge sample: 13,000 rpm, 10 minutes, 4° C.
7. Remove 400 μl supernatant and transfer to counting vial (and care must be taken not to collect any of the charcoal pellet or thin film remaining on the surface since this contains radioactive substrate).
8. Add 5 ml of cocktail for liquid scintillation counting (LSC), mix and count the sample For the determination of background radiation, a "blank" is used to determine the background signal which we have defined as the amount of $^3$H remaining in the supernatant independent of microsomal enzyme activity. Blanks are samples where PCA is added PRIOR to the addition of 180 μl reaction mixture. For newly purchased radioactive fatty acid-CoA, blanks were ~2% of the maximum signal. An increase in the blank value and a decrease in the signal magnitude is diagnostic of substrate breakdown during storage.

EXAMPLE 2

Small Volume Method

Alternatively, assays may utilize a small volume "HTS" method. The protocol for the small volume HTS method yields a total volume of 0.21 ml per assay point (0.1 ml reaction, 0.01 ml PCA and 0.1 ml charcoal). Buffer compositions are provided in Example 1.

1. To reduce total volume to 0.21 ml we have made the following changes to the assay pre-mix (volumes per assay point):
   2 μl 1.5 mM fatty acid-CoA (or a
   1 μl 1 mCi/ml radioactive $^3$H fatty acid-CoA
   10 μl 20 mM NADH
   67 μl 0.1 M PK buffer
   To make assay pre-mix for N number of assay points:
      a. multiply reagent volumes by N
      b. multiply resulting products for each reagent by 1.05 to yield a 5% "cushion"
      c. note: this cushion can be adjusted up or down depending on accuracy of liquid handling.
2. Add assay pre-mix (80 μl/assay point) to 20 μl of microsomes to initiate reaction
3. Add 10 μl of 60% PCA and vortex the sample to mix
4. Add 100 μl of charcoal suspension
5. Vigorously vortex sample to mix
6. Centrifuge sample: 13,000 rpm, 10 minutes, 4° C.
7. Remove 50 μl supernatant and transfer to counting vial (again, care was taken not to collect any of the charcoal pellet or thin film remaining on the surface due to the presence of radioactive substrate therein).
8. Add cocktail for LSC, mix and count sample

What is claimed is:

1. A process for identifying a delta-5 desaturase-modulating agent, comprising:

a) contacting a compound with a microsome, said microsome comprising a delta-5 desaturase enzyme activity, in the presence of a substrate comprising a tritium label wherein said label is bound to a delta-5 desaturase reactive carbon atom and under conditions promoting the desaturation of said substrate at said reactive carbon atom to form a double bond with said reactive carbon atom with release of tritiated water, b) determining production of said tritiated water, c) determining a difference in the amount or rate of production of said tritiated water compared to when the contacting of step (a) does not occur wherein a difference in production of tritiated water indicates modulation of said delta-5 desaturase; and thereby identifying a modulator of desaturase activity.

2. The process of claim 1, wherein said modulation is a decrease in desaturase activity.

3. The process of claim 1, wherein said modulation is an increase in desaturase activity.

4. The process of claim 1, wherein said difference of step (c) is a difference in the amount of said tritiated water detected.

5. The process of claim 1, wherein said difference of step (c) is a difference in the rate of production of said tritiated water.

6. The process of claim 1, wherein said tritium label is attached to only one of the reactive carbon atoms of a substrate molecule.

7. The process of claim 1, wherein said tritium label is attached to two reactive carbon atoms of the same substrate molecule.

8. The process of claim 1, wherein said substrate is a coenzyme A conjugate of a fatty acid having a backbone of length 20 carbon atoms.

9. The process of claim 1, wherein said substrate is a coenzyme A conjugate of a member selected from the group consisting of dihomogammalinolenic acid (DGLA, 20:3n6), 20:4n3 and 20:2n9.

10. The process of claim 9, wherein said tritium label is on carbon atom 5 and 6 of the substrate.

11. The process of claim 1, wherein said substrate is a coenzyme A conjugate of a member selected from the group consisting of 20:3n6, 20:4n3 and 20:2n9.

12. The process of claim 11, wherein said tritium label is on carbon atom 5 and 6 of the substrate.

* * * * *